US005843987A

United States Patent [19]
Rajagopalan et al.

[11] Patent Number: 5,843,987
[45] Date of Patent: Dec. 1, 1998

[54] METHOD OF STIMULATING GASTROINTESTINAL MOTILITY WITH ELLAGIC ACID

[75] Inventors: Tuticorin Govindachari Rajagopalan; Deepa Ashok Khambe, both of Bombay, India

[73] Assignee: The Procter & Gamble Company, Cincinnati, Ohio

[21] Appl. No.: 999,635

[22] Filed: Oct. 31, 1997

Related U.S. Application Data

[60] Provisional application No. 60/030,421 Oct. 31, 1996.
[51] Int. Cl.$^6$ ..................................................... A61K 31/35
[52] U.S. Cl. ................................................................ 514/453
[58] Field of Search ............................................ 514/453

[56] References Cited

U.S. PATENT DOCUMENTS

| 5,066,671 | 11/1991 | Caufield | 514/453 |
| 5,104,894 | 4/1992 | Josephy et al. | 514/455 |
| 5,137,896 | 8/1992 | Van Daele | 514/327 |
| 5,171,864 | 12/1992 | Lee | 549/222 |
| 5,229,516 | 7/1993 | Musser et al. | 546/172 |

FOREIGN PATENT DOCUMENTS

| 1 183847 | 12/1985 | Canada | C07D 211/58 |
| 0 076530 | 4/1983 | European Pat. Off. | C07D 211/58 |
| 1010-985A | 3/1987 | Japan | A61K 7/16 |

OTHER PUBLICATIONS

Bhargava et al., "Preliminary Pharmacology of Ellagic Acid from *Juglans nigra* (Black Walnut)", *J. of Pharmaceutical Sciences,* vol. 57, No. 10, pp. 1728–1732 (1968).
Press et al., "Some Physico–Chemical Properties of Ellagic Acid", *J. Appl. Chem.,* vol. 19, pp. 247–251 (1969).
Osawa et al., "Inhibition of Lipid Peroxidation by Ellagic Acid", *J. Agric. Food Chem.,* vol. 35, No. 5, pp. 808–812 (1987).
Twaij et al., Pharmacological, Phytochemical and Antimicrobial Studies on *Myrtus communis.*, *J. Biol., Sci., Res.,* vol. 19, No. 1, pp. 29–39 (1988).
Retz, "Identification of Purgative Principle of Terminalia", *The Indian J. of Pharmacy,* vol. 30, No. 10, pp. 233–234 (1968).

Teel et al., "Disposition of the Plant Phenol Ellagic Acid in the Mouse Following Oral Administration by Gavage", *Xenobiotica,* vol. 18, No. 4, pp. 397–405 (1988).
Dhingra et al., "Determination of Free Ellagic Acid by Reversed–phase High–performance Liquid Chromatography", *J. of Chromatography,* vol. 447, pp. 284–286 (1988).
Daniel et al., "Extraction, Stability, and Quantitation of Ellagic Acid in Various Fruits and Nuts", *J. of Food Composition and Analysis,* vol. 2, pp. 338–349 (1989).
Saijo et al., "Tannins and Related compounds LXXXIV. Isolation and Characterization of Five New Hydrolyzable Tannins from the Bark of *Mallotus japonicus*", *Chem. Pharm. Bull.,* vol. 37, No. 8, pp. 2063–2070 (1989).
Lin et al., "Identification and Reduction of Ellagic Acid in Muscadine Grape Juice", *J. of Food Science,* vol. 55, No. 6, pp. 1607–1609 (1990).
Wilson et al., "Quantitative Determination of Ellagic Acid", *J. Agric. Food Chem.,* vol. 38, pp. 1678–1683 (1990).
Murakami et al., "Inhibition of Gastric H+, K+–ATPase and Acid Secretion by Ellagic Acid", *Planta Med.,* vol. 57, pp. 305–308 (1991).
Daniel et al., "The Effects of pH and Rat Intestinal contents on the Liberation of Ellagic Acid From Purified and Crude Ellagitannins", *J. of Natural Products,* vol. 54, No. 4, pp. 946–952 (1991).
Sawamura et al., "Inhibitory Effects of Ellagic Acid on glucosyltransferases from Mutans Streptococci", *Biosci. Biotech. Biochem.,* vol. 56, No. 5, pp. 766–768 (1992).
Josephy et al., "Ellagic Acid and synthetic Analogues as Inhibitors of Mutagenesis and Carcinogenesis", *Cellular Targets for Chemoprevention,* 1992.
Ohemeng et al., "DNA Gyrase Inhibitory and antibacterial Activity of Some Flavones(1)", *Bioorganic & Medicinal Chem. Letters,* vol. 3, No. 2, pp. 225–230 (1993).

*Primary Examiner*—Shep K. Rose
*Attorney, Agent, or Firm*—Betty J. Zea; John M. Howell; Jacobus C. Rasser

[57] ABSTRACT

The present invention relates to the use of ellagic acid for the treatment of gastrointestinal disorders by stimulating the motility of the GI tract. In particular the present invention relates to a method of treatment of constipation, heartburn, non ulcer dyspepsia, GERD, and/or esophagitis, with a pharmaceutical composition comprising a safe and effective amount of ellagic acid or pharmaceutically acceptable salts or esters thereof. Preferably the ellagic acid is administered perorally.

23 Claims, No Drawings

METHOD OF STIMULATING GASTROINTESTINAL MOTILITY WITH ELLAGIC ACID

TECHNICAL FIELD

The present invention relates to the use of ellagic acid and pharmaceutically acceptable salts or esters thereof for the treatment or prevention of gastrointestinal disorders requiring stimulation of the motility of the gastrointestinal (GI) tract, e.g. for enhancing esophageal contractility, for stimulating gastric emptying, and for stimulating small intestinal transit time. In particular the present invention relates to a method of treatment or prevention of constipation, heartburn, NUD (non ulcer dyspepsia), GERD (gastroesophageal reflux disease), esophagitis, gastric ulcers, and/or duodenal ulcers, in a human or other animal, with a safe and effective amount of ellagic acid and pharmaceutically acceptable salts or esters thereof.

CROSS-REFERENCE

This application claims priority under Title 35, United States Code 119(e) from Provisional Application Ser. No. 60/030,421, filed Oct. 31, 1996.

BACKGROUND OF THE INVENTION

Ellagic acid, is also known as 2,3,7,8-Tetrahydroxy[1]benzopyrano-[5,4,3-cde][1]benzopyran-5,10-dione; 4,4', 5,5', 6,6'-hexahy-drodiphenic acid 2,6,2', 6'-dilactone, benzoaric acid, Lagistase, hexahydroxydiphenic acid-dilactone, and olyphenolic acid. The chemical formula is $C_{14}H_6O_8$. Ellagic acid is a naturally occurring plant phenol, occurring in its free form or in the form of ellagitannins or glucosides. It is found in certain fruits, nuts and vegetables, such as grapes, strawberries, blackberries, raspberries, cranberries, walnuts, guavas, mangoes, green tea, and pecans. It is also found in dicotyledonous plants in the genera of castenea, eucalyptus, eugenia, euphorbia, gerinimum, mangifera, platycarya, quercus, rhus and terminalia. Dhingra et al., Determination of free ellagic acid by reversed-phase high-performance liquid chromatography. *Journal of Chromatography*, 447 (1988) 284–286. Ellagic acid is present in plants as ellagitannins, which consist of a central core of glucose esterified with hexahydroxydiphenic acid. These precursor molecules may undergo hydrolysis with acid or base to yield ellagic acid. Physico-chemical properties of ellagic acid are described in: Press, Hardcastle, *J. Appl. Chem.* 19, 247 (1969).

Ellagic acid is known to possess a variety of pharmacological and biological activities. For example, ellagic acid has been reported to have antioxidant effects, antimutagenic effects, antitumor effects, blood coagulation effects, and as an inhibitor of GTase activities from *Streptococcus mutans*.

Ellagic acid has shown promise as a dietary inhibitor of carcinogenesi. It is known as a potent antagonist of polycyclic aromatic hydrocarbons, of dialkyl nitrosamines-induced mutagenesis and of the mutagenicity of bay-region diol epoxides of several aromatic hydrocarbons. Inhibition of the mutagenicity of the ultimate carcinogenic metabolite of benzo[α]pyrene-7,8-dihydrodiol-1,10-epoxide (BPDE), in the well known Ames test, is described in: A. W. Wood et al., *Proc. Nat. Acad. Sci. USA* 79, 5513 (1982). A brief discussion of ellagic acid as a prototype of a new class of cancer-preventing drugs is described in: J. Fox, *Chem. & Eng. News* 60, 26 (Oct. 25, 1982).

In addition ellagic acid was found to reduce cellular adherence of *Streptococcus mutans* to glass surface by abrogation of the enzymatic activity of glucosyltransferases (GTcases) of *Streptococcus mutans*. Sawamura et al., Inhibitory Effects of Ellagic Acid on Glucosyltransferases from Mutans Streptococci, *Biosci. Biotech Biochem.* 56(5), 766–768, 1992. Furthermore, JP 1010985, published on Jan. 13, 1989, Nippon Seifin KK, teaches GTase inhibitor, which contains ellagic acid as its active component, for addition to food and toothpaste for the inhibition of plaque in the mouth.

Furthermore, it is known that ellagic acid suffers from very poor pharmacokinetics. Particularly, ellagic acid is poorly absorbed from the gastrointestinal tract, resulting in subsequent rapid elimination. Smart et al. *Carcinogenesis* 7:1663–1667, 1986. Attempts to overcome or minimize this problem are disclosed in U.S. Pat. No. 5,104,894, Josephy et al, issued Apr. 14, 1992, University of Guelph, which teaches ellagic acid derivatives or congeners Josephy et al. teaches ellagic acid as an inhibitor of mutagenic activity and potentially as an effective agent to prevent the normal tissue toxicity caused by certain alkylating agents used in cancer chemotherapy.

Although ellagic acid is known to exhibit a variety of pharmacological and biological activities as described above, the use of ellagic acid (and salts or esters thereof) as a prokinetic agent has not been previously recognized in the art. Applicants of the present invention have surprising discovered that ellagic acid has prokinetic activity, and therefore, stimulates motility of the GI tract, enhances esophageal contractility, enhances gastric emptying, and enhances small intestinal transit time. Furthermore, applicants have surprisingly discovered that ellagic acid is useful in the treatment of constipation, heartburn, NUD (non ulcer dyspepsia), GERD (gastroesophageal reflux disease), esophagitis, gastric ulcers, and/or duodenal ulcers. In addition it is discovered that ellagic acid exhibits these effects perorally despite the fact that ellagic acid is poorly absorbed from the gastrointestinal tract.

SUMMARY OF THE INVENTION

The present invention relates to the use of ellagic acid and pharmaceutically acceptable salts or esters thereof for the treatment of gastrointestinal disorders requiring stimulation of the motility of the gastrointestinal (GI) tract, e.g. for enhancing esophageal contractility, for stimulating gastric emptying, and for stimulating small intestinal transit time. In particular the present invention relates to a method of treatment of constipation, heartburn, NUD (non ulcer dyspepsia), GERD (gastroesophageal reflux disease), esophagitis, gastric ulcers, and/or duodenal ulcers, in a human or other animal, with a safe and effective amount of ellagic acid and pharmaceutically acceptable salts or esters thereof. A "safe and effective" oral dose of ellagic acid or salts or esters thereof depends on the extent of the disease. The dosage range for the above conditions is generally from about 1 mg to about 300 mg of ellagic acid daily, preferably from about 10 mg to about 100 mg daily, more preferably about 5 mg to about 40 mg daily.

DETAILED DESCRIPTION OF THE INVENTION

The present invention relates to the use of ellagic acid and pharmaceutically acceptable salts or esters thereof for the treatment of gastrointestinal disorders requiring stimulation of the motility of the gastrointestinal (GI) tract, e.g. for enhancing esophageal contractility, for stimulating gastric emptying, and for stimulating small intestinal transit time. In particular the present invention relates to a method of treatment of constipation, heartburn, NUD (non ulcer dyspepsia), GERD (gastroesophageal reflux disease), esophagitis, gastric ulcers, and/or duodenal ulcers, in a human or other animal, with a safe and effective amount of ellagic acid and pharmaceutically acceptable salts or esters thereof. A "safe and effective" oral dose of ellagic acid or salts or esters thereof depends on the extent of the disease. The dosage range for the above conditions is generally from about 1 mg to about 300 mg of ellagic acid daily, preferably from about 10 mg to about 100 mg daily, more preferably about 5 mg to about 40 mg daily.

Ellagic acid and salts or esters thereof of the present invention, by stimulating the motility of the GI tract, act to normalize or improve/enhance the esophageal, gastric and intestinal emptying in patients suffering from decreased peristalsis of the GI tract. The usual manifestations of delayed gastric emptying include nausea, vomiting, heartburn, persistent fullness after meals and anorexia.

Ellagic acid, is also known as 2,3,7,8-Tetrahydroxy[1]benzopyrano-[5,4,3-cde][1]benzopyran-5,10-dione; 4,4', 5,5', 6,6'-hexahy-drodiphenic acid 2,6,2', 6'-dilactone, benzoaric acid, Lagistase, hexahydroxydiphenic acid-dilactone, and olyphenolic acid. The chemical formula is $C_{14}H_6O_8$.

Ellagic acid has the structure:

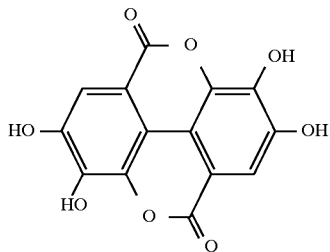

Ellagic acid is a naturally occurring plant phenol, occurring in its free form or in the form of ellagitannins or glucosides. It is found in certain fruits, nuts and vegetables, such as grapes, strawberries, blackberries, raspberries, cranberries, walnuts, guavas, mangoes, green tea, and pecans. It is also found in dicotyledonous plants in the genera of castenea, eucalyptus, eugenia, euphorbia, gerinimum, mangifera, platycarya, quercus, rhus and terminalia. Dhingra et al., Determination of free ellagic acid by reversed-phase high-performance liquid chromatography. *Journal of Chromatography*, 447 (1988) 284–286. Ellagic acid is present in plants as ellagitannins, which consist of a central core of glucose esterified with hexahydroxydiphenic acid. These precursor molecules may undergo hydrolysis with acid or base to yield ellagic acid. Physico-chemical properties of ellagic acid are described in: Press, Hardcastle, *J Appl. Chem.* 19, 247 (1969).

Methods of preparation of ellagic acid are known in the art. For example, ellagic acid can be isolated from the kino of *Eucalyptus maculata* Hook and *E. hemipholia* F. Muell., *Myrtaceae:* Gell et al., *Aust. J. Chem.* 11, 372 (1958); Hills, Carle, *ibid.* 16, 147 (1963), or prepared by sodium persulfate oxidation of gallic acid or by acid hydrolysis of crude tannin from walnuts: Perkin, Nierenstein, *J. Chem. Soc.* 87, 1412 (1905); Jurd, *J. Am. Chem. Soc.* 78, 3445 (1956); 79, 6043 (1957). Furthermore, the purification of ellagic acid is described in: Fr. Pat. 1,478,523 (1967 to Prod. Chim. Celluloses Rey), C.A. 68, 78267r (1968). All of the above references are herein incorporated by reference.

In addition ellagic acid is available in powder form from Apin Chemical, a subsidiary of Spectrum Chemical Company, United Kingdom.

The present invention relates to the use of ellagic acid for the treatment of gastrointestinal disorders requiring stimulation of gastrointestinal motility. In particular the present invention relates to a method of treatment of constipation, heartburn, non-ulcer dyspepsia, GERD, esophagitis, gastric ulcers, and/or duodenal ulcers, with a pharmaceutical composition comprising a safe and effective amount of ellagic acid and pharmaceutically acceptable salts or esters thereof.

The above disorders are more fully described in Bennett, J. R., et al., *Gastroenterology, Clinical Science and Practice,* Vol. 1, 2nd ed., pp. 82 to 84, 216 to 246, 790, 1993, which is herein incorporated by reference in it entirety.

GERD is a condition where digestive juices frequently reflux from the stomach into the lower esophagus. The irritant effect of this reflux may cause pain and dysphagia or even complications such as hemorrhage or stricture. Patients with gastroesophageal reflux disease may exhibit: 1. More frequent episodes of reflux; 2. Abnormalities of gastric function; 3. Slower esophageal emptying; 4. More irritant gastric juice; 5. Diminished mucosal resistance. If an inflammatory change occurs as a result of this reflux, then the condition can be referred to as esophagitis.

Heartburn (pyrosis) is the most common symptom of reflux of stomach juices. It is due to direct mucosal irritation by refluxed juice. The pain associated with heartburn is usually burning in character and will be felt behind the sternum, usually appearing to rise from the epigastrium and move towards or into the throat. Sometimes the pain radiates toward the back, or may be experienced entirely in the throat or epigastrium.

Non-ulcer dyspepsia ("upset stomach") generally exhibits no detectable organic cause for the symptoms. It is suggested that the symptoms are caused by abnormal motor activity in the upper gastrointestinal tract.

Chronic duodenal and gastric ulcers result in ulcerations in the epithelial cells. These are associated with acute and chronic inflammation. Evidence is developing with respect to the role of *Helicobacter pylori* in the cause of duodenal and gastric ulcers.

A limitation to the use of ellagic acid per orally is its low solubility in water or organic solvents. This property may be responsible for poor absorption of ellagic acid form the GI tract. Therefore, salts or esters of ellagic acid, which will enhance the solubility of ellagic acid are preferred for use in the method of treatment of the present invention. More preferred for use in the method of treatment of the present invention are esters of ellagic acid.

The term "pharmaceutically acceptable salts" of ellagic acid include acid-addition salts derived from either organic or inorganic acids such as acetic, formic, propionic, malonic, oxalic, tartaric, lactic, succinic, benzoic, salicylic, methanesulfonic, toluenesulfonic, hydrochloric, sulfuric or phosphoric acid, trifluoroacetate and the like, as well as alkali metal salts and sodium salt, potassium salt, magnesium salt, calcium salt, aluminum salt, piperidine salt, morpholine salt, dimethylamine salt, diethylamine salt, etc. Desired salts may be produced from other salts via conventional treatment with ion exchange resins. The term "pharmaceutically acceptable salts" means those acid-addition salts of ellagic acid which do not significantly adversely effect the pharmaceutical properties (e.g. toxicity, effectiveness, etc.) of the ellagic acid, such as are conventionally used in the pharmaceutical art.

The term "GI tract" as used herein, includes the entire digestive tract, including the esophagus, stomach, small intestine and the large intestine, e.g. the ileum, jejunum, duodenum, and the colon.

The phrase "stimulating the motility of the GI tract" as used herein means that ellagic acid or salts/esters thereof will stimulate the contractility of the muscle of the esophagus, the small intestine, the large intestine and muscle tissue there between.

Generally, the proper selection of ellagic acid or salts or esters thereof depends on the selected type of formulation, the disease pattern, especially the site and type of the disease, and the desired release of the active ingredient. In addition, the physical and chemical characteristics of ellagic acid must be taken into account when selecting suitable pharmaceutically-acceptable excipients for use in the composition of the present invention.

The method of treatment of the present invention can be accomplished by the administration of ellagic acid in a variety of dosage forms. Ellagic acid may be formulated into various pharmaceutical dosage forms for administration. Pharmaceutical compositions of the present invention comprise an effective amount of ellagic acid or pharmaceutically acceptable salts or esters thereof combined with a pharmaceutically acceptable carrier material. The pharmaceutically acceptable excipient/carrier may be selected from a wide variety of forms depending on the route of administration desired, the dosage form being an amount which is effective to stimulate gastrointestinal motility.

Pharmaceutical compositions of the present invention are preferably unitary dosage forms suitable, preferably, for administration orally, parenterally, or rectally. For oral liquid dosage forms such as suspensions, syrups, elixirs and solutions, pharmaceutically acceptable carriers include water, glycols, oils, alcohols, and the like. For solid oral dosage forms such as powders, pills, compressed tablet, hard capsule (starch or gelatin) containing beads or particles of ellagic acid, or soft gelatin capsules, pharmaceutically acceptable carriers include starches, sugars, kaolin, lubricants, binders, disintegrating agents and the like. Oral dosage forms can also be film coated, thereby masking any unpleasant taste associated with ellagic acid. For parenteral dosage forms, pharmaceutically acceptable carriers include mostly sterile water, but may also include saline solution, glucose solution or mixtures of saline and glucose solutions.

The effective oral dose of the ellagic acid or salts or esters thereof depends on the extent of the disease. The dosage range is generally from about 1 mg to about 300 mg of ellagic acid daily, preferably from about 10 mg to about 100 mg daily, more preferably about 5 mg to about 40 mg daily, and even more preferably from about 10 mg. to about 30 mg daily. This daily dose may be subdivided into multiple dosing units.

For the treatment of gastric ulcers, the effective oral dose of ellagic acid or salts or esters thereof is from about 10 mg to about 100 mg, preferably from about 20 mg to about 40 mg daily. Preferably the ellagic acid or salts/esters thereof is administered for about 8 weeks.

For the treatment of reflex esophagitis, the effective oral dose of ellagic acid or salts or esters thereof is from about 10 mg to about 50 mg, preferably from about 20 mg to about 30 mg daily, more preferably about 20 mg daily.

For the treatment of duodenal ulcers, the effective oral dose of ellagic acid or salts thereof is from about 10 mg to about 50 mg, preferably from about 20 mg to about 30 mg daily, more preferably about 20 mg daily.

For the treatment of non-ulcer dyspepsia (NUD), the effective oral dose of ellagic acid or salts or esters thereof for impaired gastric emptying is from about 20 mg to about 50 mg, preferably from about 20 mg to about 40 mg daily, more preferably 30 mg daily, and for improving GI motility about 10 mg to about 50 mg, preferably from about 10 mg to about 40 mg daily, more preferably about 15 mg to about 30 mg daily.

For the treatment of constipation, heartburn, the effective oral dose of ellagic acid or salts or esters thereof is from about 10 mg to about 50 mg, preferably from about 10 mg to about 40 mg daily, more preferably about 15 mg to about 30 mg daily.

For the treatment of gastroesophageal reflux disease, the effective oral dose of ellagic acid or salts or esters thereof is from about 10 mg to about 50 mg, preferably from about 10 mg to about 40 mg daily, more preferably about 15 mg to about 30 mg daily.

The compositions of the present invention may be given from one to six times per day, preferably from four to six times daily, more preferably up to four time daily. Each individual dose unit may contain from 1 mg to 300 mg, preferably 5 mg to 30 mg, more preferably 10 mg to 20 mg, of ellagic acid. These individual dosage units may be taken either before or after meals. Preferably for the treatment of GERD, the ellagic acid composition are administered 4 times daily, at least 15 to 30 minutes before meals and at bedtime. In general therapy is short term, usually from about 2 weeks duration to about 12 weeks duration, but can be longer.

For symptoms occurring only intermittently or at certain specific times of the day, then single daily does can be used of from about 20 mg to about 40 mg, prior to the provoking situation or condition.

The pharmaceutical compositions described herein are comprised of from about 5% to about 75%, preferably about 5% to about 50% of pharmaceutically-acceptable excipients.

The phrase "safe and effective amount," as used herein, means an amount of a compound or composition high enough to significantly modify the symptoms and/or condition to be treated, but low enough to avoid serious side effects (at a reasonable benefit/risk ratio), within the scope of sound medical judgment. The safe and effective amount of active ingredient for use in the method of the invention herein will vary with the particular condition being treated, the age and physical condition of the patient being treated, the severity of the condition, the duration of the treatment, the nature of concurrent therapy, the particular active ingredient being employed, the particular pharmaceutically-acceptable excipients utilized, and like factors within the knowledge and expertise of the attending physician, pharmacist, health care professional or other skilled artisan. The safe and effective amount of ellagic acid or salts/esters thereof means an amount that will effectively stimulate GI mobility.

Tablets and capsules are most easily administered and therefore are the more preferred dosage forms for administration in the method of the present invention.

Suitable pharmaceutical excipients, which are well-known to those skilled in the art and/or are described herein below, can be used to formulate the oral dosage forms, i.e. tablets and capsules, described herein.

The term "pharmaceutically-acceptable carrier and/or excipients" as used herein includes any physiologically inert, pharmacologically inactive material known to one skilled in the art, which is compatible with the physical and chemical characteristics of the particular active ingredients selected for use. Pharmaceutically-acceptable excipients include, but are not limited to, polymers, plasticizers, fillers, binders, disintegrants, glidants, granulating agents, lubricants, solvents, surfactants, preservatives, sweetening agents, flavoring agents, pharmaceutical grade dyes or pigments, and viscosity agents.

The term "solid oral dosage form" as used herein means any pharmaceutical composition intended to be administered to the gastrointestinal tract of an individual via the mouth of said individual. For purposes of the present invention, the delivered form can be in the form of a tablet, (preferably film-coated) containing granules or particles of active ingredients, or a capsule, containing coated beads or coated granules of the active ingredients. Capsules may include hard capsules (starch or gelatin), or soft gelatin capsules.

The term "film-coating" as used herein relates to a mixture of pharmaceutically-acceptable excipients which is applied to, combined with, mixed with or otherwise added to the active ingredients. The film coating may be applied to a compressed tablet, and/or to the beads, granules, or particles of active ingredients which are encapsulated into hard capsules (starch or gelatin), soft gelatin capsules, or compressed into tablets.

Accordingly, the film coating is preferably applied to a compressed tablet which contains particles or granules of active ingredient; however, in the event the particles or granules are themselves film-coated before being compressed into a tablet, then the film coating of the compressed tablet itself is optional. If necessary, the film coating may also be applied to the beads or small particles of active ingredient which may be encapsulated into a starch or gelatin capsule. Because of their film coating, these novel dosage forms will prohibit the undesirable taste which may accompany the use of ellagic acid or salts/esters thereof for use as the active ingredients herein. If the dosage form is a tablet, the coating also eases swallowing by providing a lubricative effect to the mouth and esophagus.

The novel solid oral dosage forms herein comprise 0% to about 2% flavoring agents. Flavoring agents among those useful herein include those described in *Remington's Pharmaceutical Sciences,* 18th Edition, Mack Publishing Company, 1990, pp. 1288–1300, incorporated by reference herein. The solid oral dosage forms herein described comprise about 0.01% to about 0.5% dyes or pigments. Among those useful herein include those dyes and pigments described in *Handbook of Pharmaceutical Excipients,* pp. 81–90, 1986 by the American Pharmaceutical Association & the Pharmaceutical Society of Great Britain, incorporated by reference herein.

Preferred granulating agents include, but are not limited to, water, ethanol, isopropanol, and acetone, or mixtures thereof. The dosage forms described herein comprise 0% to about 2% granulating agent.

The solid oral dosage forms described herein comprise about 20% to about 60% of solvent(s). A solvent(s) is preferably used if the solid oral dosage form is a soft-gelatin capsule. Preferred solvent(s) include, but are not limited to, polyethylene glycol, propylene glycol, glycerin, or mixtures thereof.

The solid oral dosage forms described herein comprise 0% to about 2% surfactants. Preferred surfactants include, but are not limited to, polyoxyethylene sorbitan fatty acid esters, sodium lauryl sulfate, sucrose monoesters and lanolin esters and ethers, and mixtures thereof.

The solid oral dosage forms described herein comprise 0% to about 2% preservatives. Preferred preservatives include, but are not limited to, alkyl esters of parahydroxybenzoic acid, benzoic acid and the salts thereof, sorbic acid and the salts thereof, benzalkonium chloride, cetylpyridinium chloride, methyl paraben, and propyl paraben, and mixtures thereof. Particularly preferred are the salts of benzoic acid, methyl paraben and propyl paraben, and mixtures thereof.

The solid dosage forms of the present invention include 0% to about 2% sweeteners. Preferred sweeteners include, but are not limited to, sucrose, glucose, saccharin, and aspartame, and mixtures thereof. Particularly preferred are sucrose and saccharin.

The concentration of fillers used in the solid oral dosage forms described herein is from about 5% to about 80%, depending upon the process used to manufacture tablets or capsules. If tablets are preferred, the filler concentration is about 5% to about 75%, preferably about 10% to about 50%. For capsules, the preferred filler concentration is about 5% to about 50%, preferably about 10% to about 30%.

Preferred fillers include, but are not limited to, lactose, compressible sugar, maltodextrin, microcrystalline cellulose, starch 1500, dicalcium phosphate, dextrose, and calcium sulfate, and mixtures thereof.

Preferred plasticizers include, but are not limited to, polyethylene glycol, propylene glycol, dibutyl phthalate, castor oil, acetylated monoglycerides, and triacetin. The compositions described herein contain from about 0.1 to about 1.0% plasticizers.

Preferred polymers include, but are not limited to, hydroxypropylmethylcellulose, hydroxypropylcellulose, and Eudragit RL®, Eudragit RS® and Eudragit NE30D® (all manufactured by Rohm Pharma GmbH, Weiterstadt, West Germany), and ethylcellulose. The compositions described herein contain from about 1% to about 5% polymers and mixtures thereof.

The solid oral dosage forms described herein comprise from about 1% to about 7% binders. Preferred binders include polyvinylpyrrolidone, hydroxypropylmethylcellulose, hydroxypropylcellulose, methylcellulose, acacia, guar gum, corn starch, maltodextrin, and starch paste, or mixtures thereof.

The oral dosage formulations described herein comprise from about 1% to about 5% disintegrants, depending on the other excipients in the formulation. The preferred disintegrants include crospovidone, crosmarmellose sodium, sodium starch glycollate, pregelatinized starch, and cornstarch, or mixtures thereof.

Glidants may be incorporated into the oral dosages forms described herein at the level of about 0.5 to about 3.0%. Preferred glidants include, but are not limited to, talc, silicone dioxide, and dicalcium phosphate.

The formulations described herein comprise from about 0.1 to about 1.5% lubricants, depending on the manufacturing process and other excipients in the formulation. Preferred lubricants include, but are not limited to, magnesium stearate, stearic acid, hydrogenated castor oil, polyethylene glycol, glyceryl behenate, and sodium laurel sulfate.

In addition to the above ingredients ellagic acid compositions may also comprise other active ingredients desirable for patients taking ellagic acid, because these patients may be suffering from multiple symptoms making additional active ingredients desirable. Additional active ingredients include the following agents.

Bismuth salts can be present in compositions, on condition that they are compatible with ellagic acid or salts or esters thereof. The methods of this invention optionally involve administration of from about 50 milligrams to about 5000 milligrams of bismuth, per day. (As used herein, the quantity of bismuth is by weight of elemental bismuth. Thus, the actual weight of a bismuth-containing compound will be greater.) Preferably, from about 500 milligrams to about 1500 milligrams of bismuth are administered, per day. The preferred duration of bismuth administration will vary according to the specific gastrointestinal disorder to be treated.

In the method of treatment of the present invention, the bismuth is preferably administered as a pharmaceutically-acceptable salt. Such bismuth salts include, for example, bismuth aluminate, bismuth subcarbonate, bismuth subcitrate, bismuth citrate, tripotassium dicitrato bismuthate, bismuth subgallate, bismuth subnitrate, bismuth tartrate, bismuth subsalicylate, and mixtures thereof. A variety of such compositions containing bismuth salts are commercially-available, including, for example, DeNol, containing tripotassium dicitrato bismuthate (sold by Gist-Brocades N.V.), Noralac, containing bismuth aluminate, alginic acid, and magnesium carbonate (manufactured by North American Pharmaceuticals), Roter bismuth, containing bismuth subnitrate (sold by Roter Laboratories), Fensobar Polvo, containing bismuth subcarbonate among other materials (manufactured by USV Pharmaceutical Corporation), and Pepto-Bismol, containing bismuth subsalicylate (sold by The Procter & Gamble Company).

A safe and effective amount of an antimicrobial can optionally be present in compositions, on condition that they are compatible with ellagic acid or salts thereof. Typically, the antimicrobial is administered at a level of from about 100 milligrams to about 10,000 milligrams, per day. The specific dosage of antimicrobial to be administered, as well as the duration of antimicrobial treatment, will depend upon such factors as the specific antimicrobial used, the pattern of the infecting organism to the antimicrobial used, the ability of the antimicrobial to reach minimum inhibitory concentrations at the site of the infection, the nature and extent of other infections (if any), the personal attributes of the subject, compliance with the treatment regimen, and the presence and severity of any side effects of the treatment.

A wide variety of antimicrobials are useful in this invention. As used herein, such "antimicrobials" refer to any naturally-occurring, synthetic or semi-synthetic compound or composition, or mixture thereof, which is safe for human use as used in the processes of this invention, and is effective in killing or substantially inhibiting the growth of microbes when used in the processes of this invention. Antibiotics are among the preferred antimicrobials useful herein. Such antibiotics can be generally classified by chemical composition, into the following principal groups: the aminoglycosides, such as gentamicin, neomycin, kanamycin, the streptomycin; the macrolides, such as erythromycin, clindamycin, and rifampin, the penicillins, such as penicillin G, penicillin V, ampicillin and amoxycillin; the polypeptides, such as bacitracin and polymyxin; the tetracyclines, such as tetracycline, chlortetracycline, oxytetracycline, and doxycycline; the cephalosporins, such as cephalexin and cephalothin; and such miscellaneous antibiotics as chloramphenicol and clindamycin. These antibiotics can be generally said to function in one of four ways: inhibition of cell walls synthesis, alteration of cell wall permeability, inhibition of protein synthesis, or inhibition of nucleic acid synthesis.

Other optional antimicrobials useful herein include the sulfonamides; nitrofurans, such as nitrofurazone nitrofurantoin, and furazolidone; and metronidazole, tinidazole, and nimorazole. Antimicrobials among those useful herein are described in the following publications, which are incorporated herein by reference: *Remington's Pharmaceutical Sciences* (15th edition 1975); F. H. Meyers, et al., *Review of Medical Pharmacology* (7th edition 1980); *Gaddum's Pharmacology* (8th edition 1978); and A. Goodman, A. G. Goodman and L. S. Gilman, *The Pharmacological Basis of Therapeutics* (6th edition 1980).

Optionally, a sample of the microbe is obtained from the stomach of the subject to be treated, as by biopsy, aspiration, or by other suitable method, and the organism cultured and tested for sensitivity to the various antimicrobials useful herein. Preferably such sensitivity testing is by determination of the relative minimum inhibitory concentrations of the antimicrobials using broth and plate dilution techniques. The antimicrobial found to be most effective against the cultured bacteria (i.e., effective at the lowest minimum inhibitory concentration) is then selected for use in the methods of this invention.

Combinations of bismuth and antimicrobials can optionally be used in the methods of the present invention. For example, U.S. Pat. No. 5,256,684, issued Oct. 26, 1993, Marshall, teaches particular combinations of bismuth and an antimicrobial for the treatment of gastrointestinal disorders, in particular, gastrointestinal disorders of the upper GI tract that are caused or mediated by bacteria, including campylobacter-like organisms, e.g. *campylobacter pyloridis*. Specifically this reference teaches the administration of about 50 about 5000 mg of bismuth daily for from 3 to 56 day, and administering a safe and effective amount of an antimicrobial daily for from 1 to 21 days. This reference is incorporated herein by reference in its entirety.

Antiinflammatory agents can be present in oral compositions, on condition that they are compatible with ellagic acid or salts or esters thereof. Such agents may include, but are not limited to, non-steroidal antiinflammatory agents such as ketorolac, flurbiprofen, ibuprofen, naproxen, indomethacin, aspirin, ketoprofen, piroxicam and meclofenamic acid. If present, the antiinflammatory agents generally comprise from about 0.001% to about 5% by weight of the composition.

Nutrients can also be present in the compositions of the present invention, on condition that they are compatible with the ellagic acid or salts thereof. Such agents include, but are not limited to folate, retinoids (Vitamin A), Vitamin C, Vitamin E and zinc. If present, nutrients generally comprise from about 0.001% to about 10% by weight of the composition.

All percentages used herein are by weight of the composition unless otherwise indicated.

The following non-limiting methods of treatment and compositions, in unit dosage form, further illustrate the novel methods of treatment of the present invention.

Typical formulations of unit dosage forms of ellagic acid are as follows:

EXAMPLE 1

Examples of oral solutions of the present invention are made by conventional processes by mixing the following:

| Ingredient | (Wt. %) |
| --- | --- |
| Ellagic Acid | 0.01–0.1% |
| Propylene Glycol | 10% |
| Sugar Syrup | 60% |
| Sodium Saccharin | 0.01% |

| Ingredient | (Wt. %) |
|---|---|
| Flavours | q.s. |
| Water purified q.s. to | 100% |

EXAMPLE 2

Examples of uncoated tablets of the present invention, each weighing 172 mg to 262 mg, are made by conventional processes by mixing the following ingredients and compressing into tablets:

| Ingredient | |
|---|---|
| Ellagic Acid | 10–100 mg |
| Lactose | 100 mg |
| Maize Starch | 50 mg |
| Polyvinyl Pyrrolidone | 5 mg |
| Talcum | 5 mg |
| Magnesium stearate | 2 mg |

EXAMPLE 3

Examples of controlled release tablets, each weighing approximately 100 mg to 190 mg, of the present invention are made by conventional processes by mixing the following ingredients, compressing into tablets, and thereafter coating the tablet cores:

| Ingredient | |
|---|---|
| Core: | |
| Ellagic Acid | 10–100 mg |
| Lactose | 10 mg |
| Microcrystalline Cellulose (Avicel pH 101) | 20 mg |
| Release regarding Hydrogel Polymer | 50 mg |
| Talcum | 2 mg |
| Magnesium stearate | 1 mg |
| Coat: | |
| Hydroxy Propyl Methyl Cellulose | 5 mg. |
| Polyethylene Glycol 6000 | 0.55 mg |
| Talcum | 0.5 mg |
| Titanium dioxide | 0.01 mg |
| Colour | q.s. |

EXAMPLE 4

Examples of suspensions of the present invention are made by conventional processes by mixing the following:

| Ingredient | (Wt. %) |
|---|---|
| Ellagic Acid | 0.01–0.1% |
| Methyl cellulose | 0.5% |
| Xanthan gum | 0.2% |
| Surfactant | 0.01% |
| Sorbitol liquid | 30.00% |
| Preservatives | 0.1% |
| Stabilizers | 0.1% |
| Sugar syrup q.s. to | 100.00% |

EXAMPLE 5

Examples of parenteral solutions of the present invention are made by conventional processes by mixing the following:

| Ingredient | (Wt. %) |
|---|---|
| Ellagic Acid | 0.01–0.1% |
| Propylene Glycol | 10% |
| Chlorocresol | 0.1% |
| Water for injection q.s. to | 100% |

EXAMPLE 6

An examples of a suppository of the present invention are made by conventional processes by mixing and pouring into a mold, the following:

| Ingredients | (Wt. %) |
|---|---|
| Ellagic Acid | 0.1% |
| Polyethylene Glycol 400 | 29.89% |
| Polyethylene Glycol 6000 | 70% |
| Surfactant (Span) | 0.01% |

EXAMPLE 7

A human subject, suffering from gastric ulcers, is treated by a method of the present invention. The subject is first diagnosed with gastric ulcers. The subject is then treated according to the method of the present invention by administering a compressed tablet comprising 20 mg of ellagic acid twice a day for 8 weeks.

EXAMPLE 8

A human subject, suffering from constipation, is treated by a method of the present invention. The subject is first diagnosed with constipation. The subject is then treated according to the method of the present invention by administering a compressed tablet comprising 10 mg of ellagic acid as needed until the constipation is relieved.

EXAMPLE 9

A human subject, suffering from reflex esophagitis, is treated by a method of the present invention. The subject is first diagnosed with reflex esophagitis. The subject is then treated according to the method of the present invention by administering a compressed tablet comprising 10 mg of ellagic acid 3 times daily before meals, until the reflex esophagitis is relieved.

EXAMPLE 10

A human subject, suffering from GERD, is treated by a method of the present invention. The subject is first diagnosed with GERD. The subject is then treated according to the method of the present invention by administering a compressed tablet comprising 10 mg of ellagic acid 4 times daily at least 10 to 30 minutes before meals and at bedtime, for 2 to 12 weeks.

While particular embodiments of the present invention have been described, it will be obvious to those skilled in the art that various changes and modifications to the present invention can be made without departing from the scope and spirit of the present invention. It is intended to cover, in the appended claims, all such modifications that are within the scope of the present invention.

What is claimed is:

1. A method of stimulating the motility of the GI tract by administering, perorally, rectally or intravenously, a safe and effective amount of ellagic acid and pharmaceutically acceptable salts or esters thereof, to a human or other animal.

2. The method of claim 1 wherein the ellagic acid is administered perorally.

3. The method of claim 2 wherein the dosage of ellagic acid or a pharmaceutically acceptable salt or ester thereof is from about 1 mg to about 300 mg daily.

4. The method of claim 3 wherein the dosage of ellagic acid or a pharmaceutically acceptable salt or ester thereof is from about 10 mg to about 100 mg daily.

5. The method of claim 4 wherein the dosage of ellagic acid or a pharmaceutically acceptable salt or ester thereof is from about 5 mg to about 40 mg daily.

6. The method of claim 5 wherein the duration of treatment is from about 2 weeks to about 12 weeks.

7. A method of treating or preventing gastrointestinal disorders by stimulating the motility of the GI tract through administration, perorally, rectally or intravenously, of a safe and effective amount of ellagic acid and pharmaceutically acceptable salts or esters thereof, to a human or other animal.

8. The method of claim 7 wherein the ellagic acid is administered perorally.

9. The method of claim 8 wherein the dosage of ellagic acid or a pharmaceutically acceptable salt or ester thereof is from about 1 mg to about 300 mg daily.

10. The method of claim 9 wherein the dosage of ellagic acid or a pharmaceutically acceptable salt or ester thereof is from about 10 mg to about 100 mg daily.

11. The method of claim 10 wherein the dosage of ellagic acid or a pharmaceutically acceptable salt or ester thereof is from about 5 mg to about 40 mg daily.

12. The method of claim 11 wherein the duration of treatment is from about 2 weeks to about 12 weeks.

13. A method of treating or preventing constipation, heartburn, non-ulcer dyspepsia, gastroesophageal reflux disease, and esophagitis by stimulating the motility of the G.I. tract through the administration perorally, rectally or intravenously, of a safe and effective amount of ellagic acid and pharmaceutically acceptable salts or esters thereof, to a human or other animal.

14. The method of claim 13 wherein the ellagic acid is administered perorally.

15. The method of claim 14 wherein the dosage of ellagic acid or a pharmaceutically acceptable salt or ester thereof is from about 1 mg to about 300 mg daily.

16. The method of claim 15 wherein the dosage of ellagic acid or a pharmaceutically acceptable salt or ester thereof is from about 10 mg to about 100 mg daily.

17. The method of claim 16 wherein the dosage of ellagic acid or a pharmaceutically acceptable salt or ester thereof is from about 5 mg to about 40 mg daily.

18. The method of claim 17 wherein the duration of treatment is from about 2 weeks to about 12 weeks.

19. The method of claim 14 wherein the dosage of ellagic acid or pharmaceutically acceptable salt or ester thereof is from about 15 mg to about 30 mg daily for the treatment of constipation.

20. The method of claim 14 wherein the dosage of ellagic acid or pharmaceutically acceptable salt or ester thereof is from about 20 mg to about 40 mg daily for the treatment of non-ulcer dyspepsia with impaired gastric emptying.

21. The method of claim 14 wherein the dosage of ellagic acid or pharmaceutically acceptable salt or ester thereof is from about 15 mg to about 30 mg daily for the treatment of non-ulcer dyspepsia to improve GI motility.

22. The method of claim 14 wherein the dosage of ellagic acid or pharmaceutically acceptable salt or ester thereof is from about 15 mg to about 30 mg daily for the treatment of gastroesophageal reflux disease.

23. The method of claim 14 wherein the dosage of ellagic acid or pharmaceutically acceptable salt or ester thereof is from about 20 mg to about 30 mg daily for the treatment of esophagitis.

* * * * *